(12) United States Patent
Darley et al.

(10) Patent No.: US 11,439,821 B2
(45) Date of Patent: Sep. 13, 2022

(54) TRANSFORMABLE SPEECH PROCESSOR MODULE FOR A HEARING PROSTHESIS

(71) Applicant: Cochlear Limited, Macquarie University (AU)

(72) Inventors: Derek Ian Darley, Cromer Heights (AU); Michael Goorevich, Naremburn (AU); Peter Scott Single, Lane Cove (AU)

(73) Assignee: Cochlear Limited, Macquarie University (AU)

( * ) Notice: Subject to any disclaimer, the term of this patent is extended or adjusted under 35 U.S.C. 154(b) by 733 days.

(21) Appl. No.: 15/874,774

(22) Filed: Jan. 18, 2018

(65) Prior Publication Data
US 2018/0160244 A1   Jun. 7, 2018

Related U.S. Application Data

(60) Division of application No. 14/712,333, filed on May 14, 2015, now Pat. No. 9,906,881, which is a
(Continued)

(30) Foreign Application Priority Data

Dec. 24, 2003   (AU) .............................. 2003907138

(51) Int. Cl.
*A61N 1/36* (2006.01)
*H04R 25/00* (2006.01)
*H04R 25/02* (2006.01)
*H04R 1/02* (2006.01)
(Continued)

(52) U.S. Cl.
CPC ........... *A61N 1/36038* (2017.08); *H04R 1/02* (2013.01); *H04R 1/1091* (2013.01); *H04R 25/02* (2013.01);
(Continued)

(58) Field of Classification Search
CPC ........ H04R 25/65; H04R 1/02; H04R 1/1091; H04R 25/606; H04R 25/02; H04R 25/60;
(Continued)

(56) References Cited

U.S. PATENT DOCUMENTS

| 4,347,956 A | 9/1982 | Berger |
| 4,819,647 A | 4/1989 | Byers et al. |

(Continued)

FOREIGN PATENT DOCUMENTS

| DE | 3723809 A1 | 1/1989 |
| DE | 10228828 C1 | 10/2003 |

(Continued)

OTHER PUBLICATIONS

International Search Report and Written Opinion for PCT/US04/43288, dated Jun. 1, 2005.
(Continued)

*Primary Examiner* — Mark W. Bockelman
(74) *Attorney, Agent, or Firm* — Pilloff Passino & Cosenza LLP; Martin J. Cosenza

(57) ABSTRACT

A method for operating an external component of a cochlear implant hearing system. The external component includes a speech processor module operable in a stand-alone mode of operation and a body-worn mode of operation, and a protective case. The method includes operating the speech processor module in the stand-alone mode, determining when the speech processor module is mounted in the case, and operating the speech processor module in the body-worn mode in response to determining that the speech processor module is mounted in the case.

28 Claims, 8 Drawing Sheets

Related U.S. Application Data continuation of application No. 14/243,862, filed on Apr. 2, 2014, now abandoned, which is a continuation of application No. 13/729,485, filed on Dec. 28, 2012, now abandoned, which is a continuation of application No. 12/703,160, filed on Feb. 9, 2010, now Pat. No. 8,352,037, which is a division of application No. 10/586,524, filed as application No. PCT/US2004/043288 on Dec. 27, 2004, now Pat. No. 7,660,633.

(51) Int. Cl.
*H04R 1/10* (2006.01)
*A61N 1/378* (2006.01)

(52) U.S. Cl.
CPC .......... *H04R 25/60* (2013.01); *H04R 25/603* (2019.05); *H04R 25/606* (2013.01); *H04R 25/65* (2013.01); *A61N 1/3787* (2013.01); *H04R 25/604* (2013.01); *H04R 25/607* (2019.05); *H04R 2225/021* (2013.01); *H04R 2225/31* (2013.01); *H04R 2225/49* (2013.01); *H04R 2225/57* (2019.05); *H04R 2225/67* (2013.01); *H04R 2460/13* (2013.01)

(58) Field of Classification Search
CPC .............. H04R 2460/13; H04R 25/604; H04R 2225/021; H04R 2225/31; H04R 2225/49; H04R 2225/67; A61N 1/36032; A61N 1/3787
See application file for complete search history.

(56) References Cited

U.S. PATENT DOCUMENTS

| | | | |
|---|---|---|---|
| 4,918,737 A | 4/1990 | Luethi | |
| 5,204,917 A | 4/1993 | Arndt et al. | |
| 5,603,726 A | 2/1997 | Schulman et al. | |
| 5,824,022 A | 10/1998 | Zilberman et al. | |
| 5,948,006 A | 9/1999 | Mann | |
| 6,272,382 B1 | 8/2001 | Faltys et al. | |
| 6,532,295 B1 | 3/2003 | Brimhall et al. | |
| 6,748,093 B2 | 6/2004 | Topholm | |
| 6,761,266 B2 | 7/2004 | Popish | |
| 7,003,128 B2 | 2/2006 | Boonen | |
| 7,113,611 B2 | 9/2006 | Leedom et al. | |
| 7,123,733 B1 | 10/2006 | Borowsky et al. | |
| 7,171,014 B2 | 1/2007 | Morales et al. | |
| 7,630,772 B1 | 12/2009 | Walsh et al. | |
| 7,660,633 B2 | 2/2010 | Darley et al. | |
| 8,068,914 B1 | 11/2011 | Walsh et al. | |
| 8,155,748 B1 | 4/2012 | Walsh et al. | |
| 8,352,037 B2 | 1/2013 | Darley et al. | |
| 2004/0052388 A1 | 3/2004 | Niederdrank | |
| 2007/0106344 A1 | 5/2007 | Darley et al. | |
| 2008/0288022 A1 | 11/2008 | Van der Borght et al. | |
| 2010/0137942 A1 | 6/2010 | Darley et al. | |
| 2013/0274826 A1 | 10/2013 | Darley et al. | |
| 2015/0025595 A1 | 1/2015 | Darley et al. | |
| 2015/0051667 A1 | 2/2015 | Van Der Borght et al. | |
| 2015/0249897 A1 | 9/2015 | Darley et al. | |
| 2016/0296755 A1 | 10/2016 | Van Der Borght et al. | |

FOREIGN PATENT DOCUMENTS

| | | |
|---|---|---|
| WO | 01087014 A3 | 11/2001 |
| WO | 03076012 A1 | 9/2003 |
| WO | 2005062668 A1 | 7/2005 |

OTHER PUBLICATIONS

Supplementary European Search Report for Europe Application No. EP 04815373.8 dated Aug. 16, 2010.

TRANSFORMABLE SPEECH PROCESSOR MODULE FOR A HEARING PROSTHESIS

CROSS-REFERENCE TO RELATED APPLICATIONS

This application is a divisional of U.S. application Ser. No. 14/712,333, filed May 14, 2015, which is a continuation application of U.S. application Ser. No. 14/243,862 filed Apr. 2, 2014, which is a continuation application of U.S. application Ser. No. 13/729,485 filed Dec. 28, 2012, which is a continuation application of U.S. application Ser. No. 12/703,160 filed Feb. 9, 2010, now U.S. Pat. No. 8,352,037, which is a divisional of U.S. application Ser. No. 10/586,524, filed Oct. 23, 2006, which is a National Stage of International Application No. PCT/US2004/043288, filed Dec. 27, 2004, which claims priority benefit of Australian Provisional Patent Application No. 2003907138, filed Dec. 24, 2003. The content of these applications is hereby incorporated by reference herein in their entirety.

BACKGROUND

Field of the Invention

The present invention relates to a hearing prosthesis and, more particularly, a transformable speech processor module for a hearing prosthesis.

Related Art

The use of medical devices to provide therapy to individuals for various medical conditions has become more widespread as the advantages and benefits of such devices become more widely appreciated and accepted throughout the population. In particular, devices such as implantable pacemakers, defibrillators, functional electrical stimulation devices such as hearing prostheses, organ assist or replacement devices, and other medical devices, have been successful in performing life saving and/or lifestyle enhancement functions for a number of individuals.

Many such medical devices often include one or more sensors, processors, controllers or other functional electrical components that are permanently or temporarily implanted in a patient. Many such implantable devices require the transcutaneous transfer of power and/or information with external components that are part of, or operate in conjunction with, the implanted components of the medical device. Such external components are typically removably attached to the body of the patient.

One such type of medical device is a cochlear implant system, also commonly referred to as a cochlear prosthesis. Cochlear implant systems provide the benefit of hear to individuals suffering from severe to profound hearing loss. Hearing loss in such individuals is due to the absence or destruction of the hair cells in the cochlea which transduce acoustic signals into nerve impulses. Cochlear implants essentially simulate the cochlear hair cells by directly delivering electrical stimulation to the auditory nerve fibers. This causes the brain to perceive a hearing sensation resembling the natural hearing sensation normally delivered to the auditory nerve.

Conventional cochlear implant systems primarily include an external assembly directly or indirectly attached to the body of the patient (referred to herein as the recipient), and an internal assembly which is implanted in the patient. The external assembly typically comprises one or more microphones for detecting sound, a speech processing unit that converts detected sound, particularly speech, into an electrical coded signal, a power source, and an external transcutaneous transfer coil. The internal assembly typically comprises an internal transcutaneous transfer coil, a stimulator unit located within a recess of the temporal bone of the recipient, and an electrode array positioned in the recipient's cochlear.

Collectively, the external coil and the internal coil form an inductively-coupled transcutaneous transfer system. The transfer of energy via this system is controlled to effect the transmission of the electrical coded signals, referred to herein as stimulation signals, and power signals from the external speech processing unit to the implanted stimulator unit. Similarly, the transcutaneous transfer system may be used to effect the transmission of telemetry data from the implanted stimulator unit to the exterior speech processing unit. Conventionally, the communications link has been in the form of a radio frequency (RF) link, although other such links have been proposed and implemented. Once a stimulation signal has been transmitted to the implanted transcutaneous transfer coil, it is provided to the implanted stimulator unit which processes the signal and outputs one or more signals to the intra-cochlear electrode assembly which applies the electrical stimulation directly to the auditory nerve of the recipient.

The speech processor unit has traditionally been worn on the body, such as by being attached to clothing, or by being supported on the ear of the recipient. This latter configuration is commonly referred to as a BTE (behind the ear) configuration. The speech processor unit is relatively expensive and susceptible to damage, especially in the hands of infants or small children, or when used in an unsuitable environment.

SUMMARY

In one aspect of the invention, a method for operating an external component of a cochlear implant hearing system is disclosed. The external component comprises a speech processor module is operable in a stand-alone mode of operation and a body-worn mode of operation, and a protective case. The method comprises operating the speech processor module in the stand-alone mode, determining when the speech processor module is mounted in the case, and operating the speech processor module in the body-worn mode in response to determining that the speech processor module is mounted in the case.

In another aspect of the invention, a method for operating a cochlear implant hearing system is disclosed. The method comprises operating, in a stand-alone mode of operation, a speech processor module having processing circuitry disposed in a housing, determining, via an operational mode controller, when the speech processor module is mounted in a protective case, and operating the speech processor module in a body-worn mode of operation in response to determining that the speech processor module is mounted in the case.

DETAILED DESCRIPTION

Embodiments of the present invention are directed to a speech processor module which may be implemented in more than one mode of operation of a hearing prosthesis. Specifically, certain embodiments of the present invention are directed to a speech processor module that can be implemented as a component of in a behind-the-ear (BTE) speech processing unit, and as a component of a body-worn speech processing unit. The present invention is also directed to an external component system for a hearing prosthesis that enables the dual-mode speech processor module to be worn on the body of a recipient rather than behind the recipient's ear.

Advantageously, certain embodiments of certain aspects of the present invention can be implemented such that the dual-mode speech processor module is protected from adverse environmental conditions, including certain recipients. For example, in some embodiments described herein, the external component system includes a protective case which protects the speech processor module from infants, small children, mentally handicapped, etc., and/or allows the use of the speech processor module in environments traditionally considered to be unsuitable for prosthetic hearing devices. As a result, embodiments of the present invention enable hearing prostheses to be worn by a wide range of recipients in a wide range of environments.

Embodiments of the present invention are described below in connection with one embodiment of an exemplary hearing prosthesis, a cochlear prosthesis (also referred to as a cochlear implant system, cochlear prosthetic device and the like; "cochlear implant system" herein). Cochlear implant systems use direct electrical stimulation of auditory nerve cells to bypass absent or defective hair cells that normally transducer acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, a cochlear implant system provides stimulation of the cochlear nucleus in the brainstem.

Figure 1A:
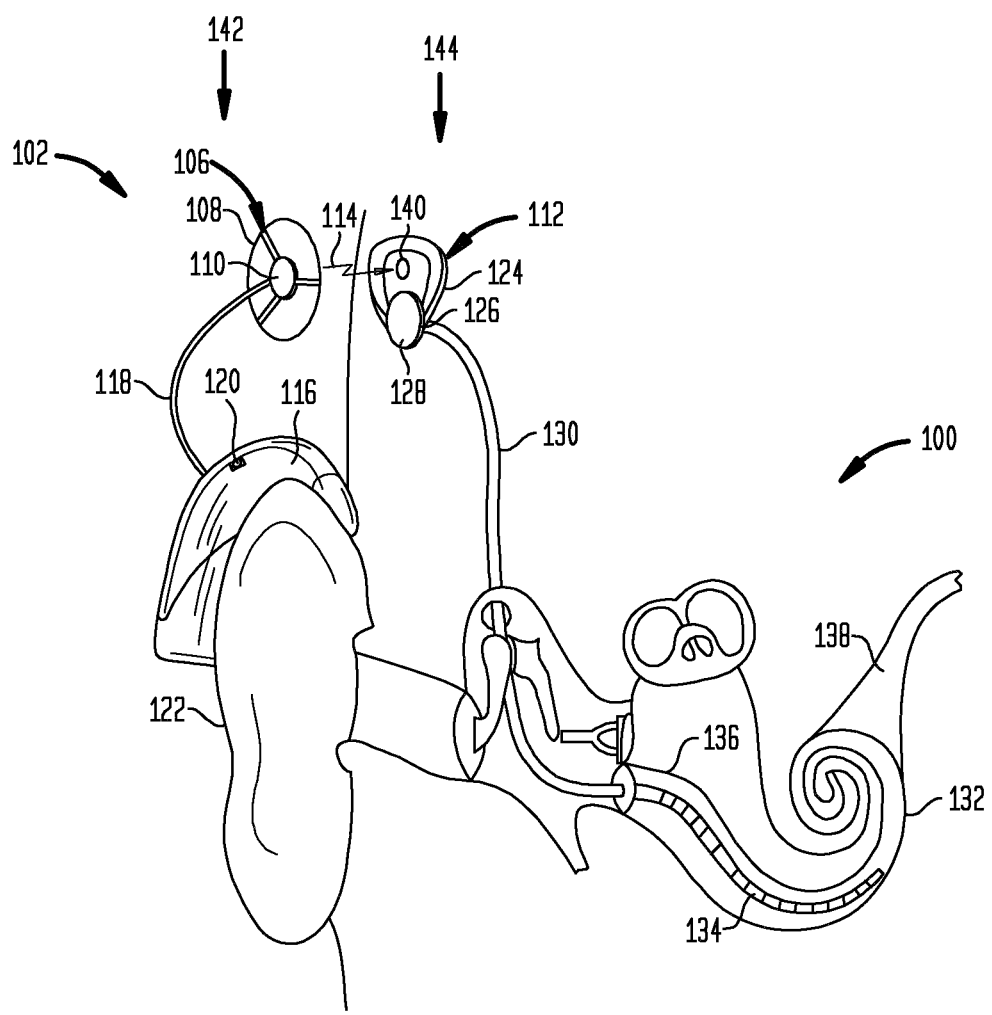
FIG. 1A is a perspective view of one embodiment of a hearing prosthesis in which embodiments of the present invention may be advantageously implemented.

FIG. 1A is a schematic diagram of an exemplary cochlear implant system 100 in which embodiments of the present invention may advantageously be implemented. Cochlear implant system 100 comprises external component assembly 142 which is directly or indirectly attached to the recipient, and an internal component assembly 144 which is temporarily or permanently implanted in the recipient. External component assembly 142 typically comprises a microphone 120 for detecting sound, a speech processing unit 116, a power source (not shown), and an external transmitter unit 106. External transmitter unit 106 comprises an external coil 108, and preferably, an alignment magnet 110 secured directly or indirectly to external coil 108. Speech processing unit 116 processes the output of microphone 120 that are positioned, in the depicted example, by the ear 122 of the recipient. Speech processing unit 116 generates coded signals, referred to herein as a stimulation data signals, which are provided to external transmitter unit 106 via cable 118.

Internal components 144 comprise an internal receiver unit 112, a stimulator unit 126, and an electrode array 134. Internal receiver unit 112 comprises an internal transcutaneous transfer coil 124, and preferably, an alignment magnet 140 fixed relative to internal coil 124. Internal receiver unit 112 and stimulator unit 126 are hermetically sealed within a housing 128. Internal coil 124 receives power and data from external coil 108. A cable 130 extends from stimulator unit 126 to cochlea 132 and terminates in electrode array 134. Signals generated by stimulator unit 126 are applied by array 134 to the basilar membrane 136, thereby stimulating the auditory nerve 138.

Collectively, external coil 108 and internal coil 124 form an inductively-coupled coil system of a transcutaneous transfer apparatus 102. In one embodiment, external coil 108 transmits and receives electrical signals to/from internal coil 124 via a radio frequency (RF) link 114. In use, implantable receiver unit 112 may be positioned in a recess of the temporal bone adjacent ear 122 of the recipient.

Figure 1B:
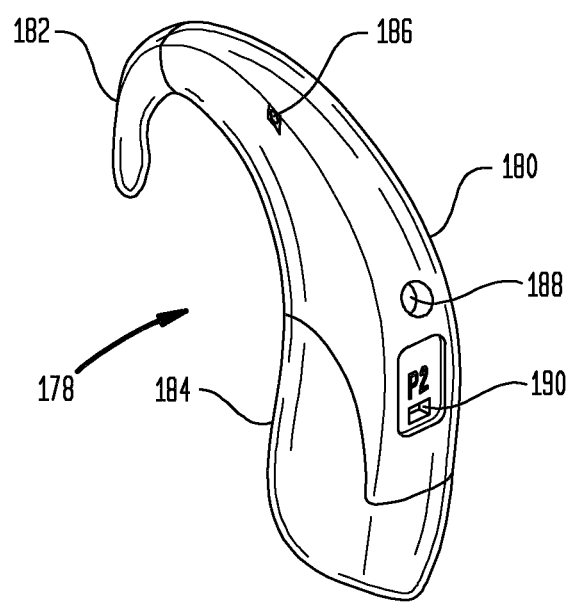
FIG. 1B is a perspective view of one embodiment of a dual mode speech processing unit in accordance with one embodiment of the present invention.

As noted, embodiments of the present invention are directed to a speech processor module which may be implemented in more than one mode of operation in a hearing prosthesis such as cochlear implant system 100. FIG. 1B is a perspective view of one embodiment of a dual-mode speech processor module of the present invention. In this embodiment, the dual-mode speech processor module of the present invention is configured to be used in a behind-the-ear (BTE) speech processing unit 178, similar to speech processing unit 116 illustrated in FIG. 1A.

Behind the ear (BTE) speech processing unit 178 comprises a speech processor module 180 that contains signal processing circuitry (not shown). A detachable ear hook 182 is provided at one end of speech processor module 180 so as to allow the speech processor to be supported behind the outer ear of the recipient of the cochlear implant system. A detachable power supply 184 comprising a rechargeable battery or other power source (not shown) is attached to speech processor module 180 to provide power to the module. Speech processor module 180 utilizes a built-in microphone 186 that generates signals to the signal processing circuitry housed within the speech processor module. Built-in microphone 186 is also referred to as internal microphone 186 herein.

Speech processor module 180 includes a headpiece connector 188 and an accessories connector 190 to connect to other components of the implementing cochlear implant system or other hearing prosthesis. In operation, cables with an appropriately configured connector extends from speech processing module 180 to a headpiece and, possible, an accessory device, as described in detail below.

Speech processing unit 178 is configured to operate in a stand-alone manner; that is, as a behind-the-ear (BTE) speech processing unit. However, speech processing unit 178 is susceptible to damage from rough handling, such as might be experienced when used by infants or small children. It also may not be suitable for use in adverse environments, such as environments having airborne particulates or significant moisture. To operate under such conditions, speech processor module 180 can operate in a body-worn mode of operation in an external component system.

Figure 2:
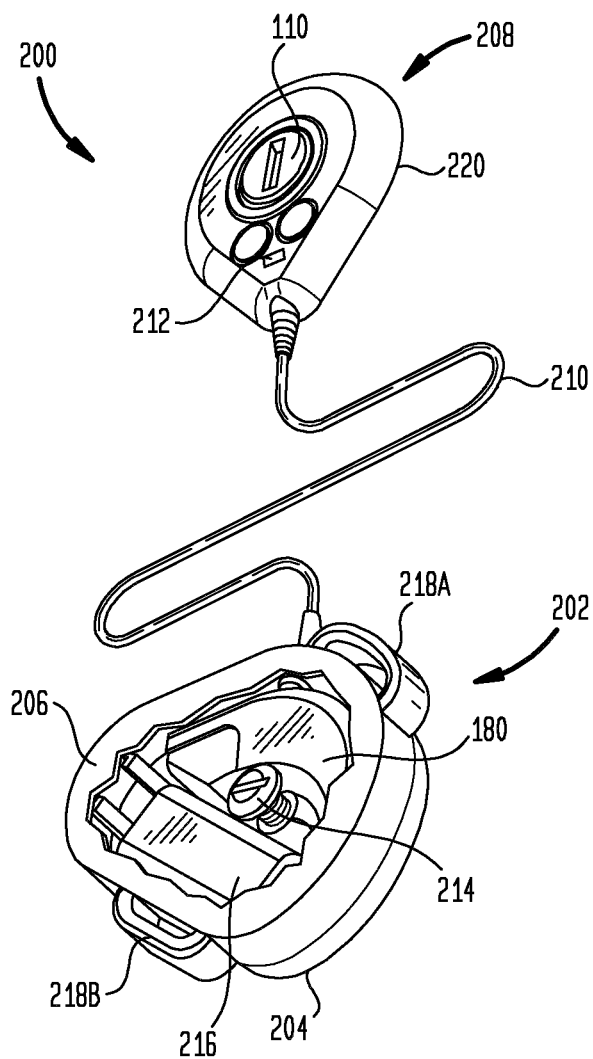
FIG. 2 is a perspective view of an external component system of a hearing prosthesis according to one embodiment of the present invention suitable for use with the speech processing unit illustrated in FIG. 1B.
Figure 3:
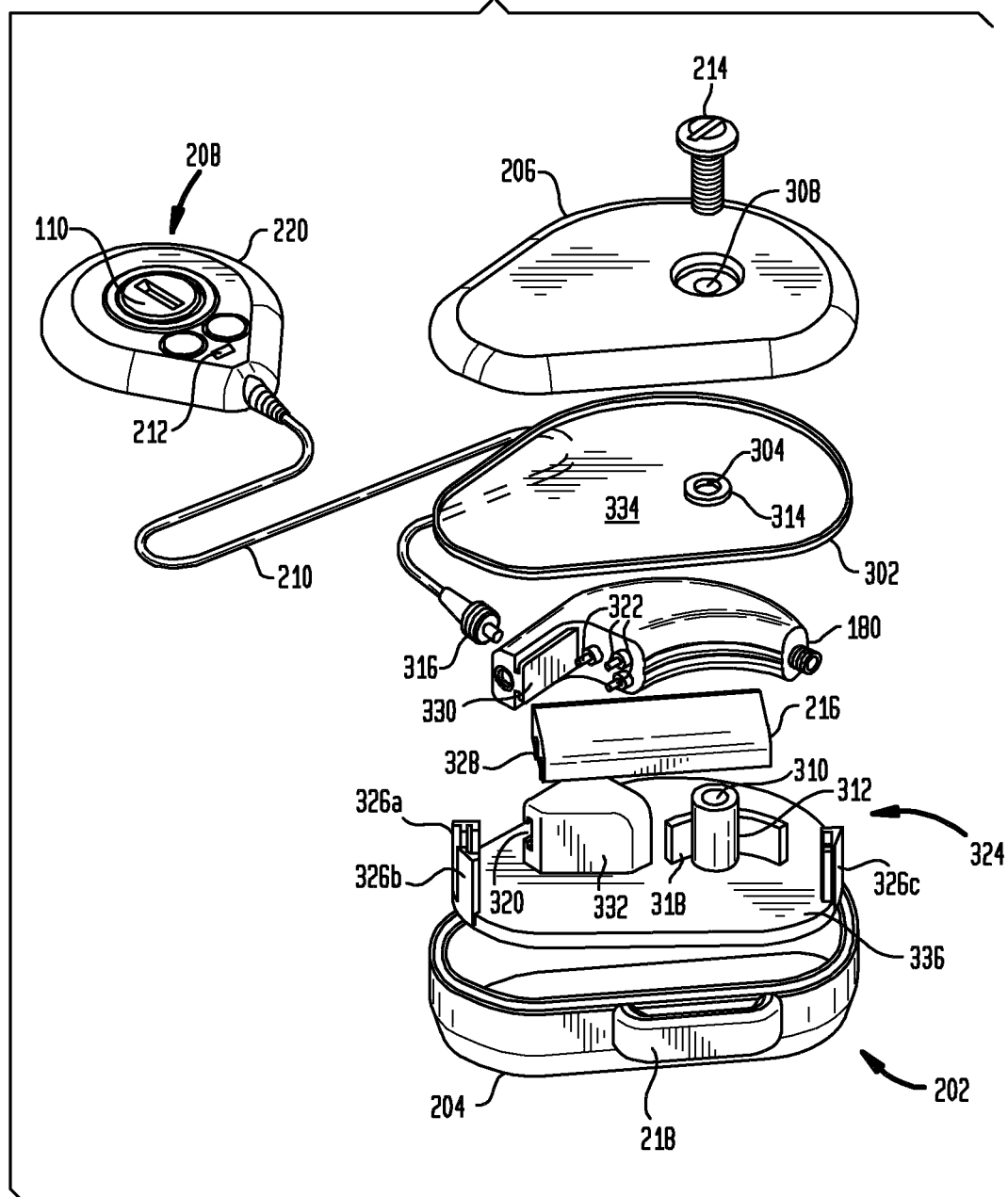
FIG. 3 is an exploded perspective view of the embodiment of illustrated in FIG. 2.

One embodiment of an external component system 200 of a hearing prosthesis according to the present invention is depicted in FIGS. 2 and 3. External component system 200 operationally replaces external component assembly 142 of cochlear implant system 100 illustrated in FIG. 1A to convert the cochlear implant system from a prosthesis which may be readily damaged by the recipient and/or environment, to one which is more robust or rugged and, therefore, suitable for use by infants, children, mentally handicapped and other recipients, and/or worn by any recipient in one or more adverse environmental conditions.

In certain embodiments, external component system 200 provides protection for speech processor module 180. In the embodiment shown in FIG. 2, for example, a protective case 202 is included in external component system 200 to house speech processor module 180 and an on-board power supply 216. In certain embodiments, such protection includes protecting these components from ingress of fluid such as water. In one embodiment, for example, protective case 202 is fluid resistant. In another embodiment, protective case 202 prevents substantially all fluid ingress, even at elevated atmospheric pressure. Similarly, in certain embodiments, protective case 202 is at least resistant to the ingress of dust or other particulates such as airborne fumes. In other embodiments, protective case 202 is capable of providing protection against shocks and vibration, electromagnetic interference (EMI) and other environmental conditions which may adversely affect the operational performance, integrity, and/or lifespan of speech processor module 180.

External component system 200 also comprises a one-piece headpiece 208 communicably coupled to speech processor module 180 via a cable 210. As will be described in greater detail below, headpiece 208 comprises the above-noted external transmitter unit 106 including external coil 108, and alignment magnet 110 mounted in a protective housing 220 that provides the same or similar protection of its components as protective case 202.

Protective case 202 comprises a base member 204 and a cover member 206 which mechanically mate with each other to form a protective enclosure in which speech processor module 180 is secured. Protective case 202 also comprises a tray 324 on which speech processor module 180 is removably mounted. In addition, tray 324 is configured to have on-board power supply 216 mounted adjacent to speech processor module 180 to provide power to the speech processor module as described herein. These and other components of protective case 202 are described in further detail below.

Referring again to FIG. 1B, speech processor module 180 is configured to be connected to a detachable power supply 184 when implemented in a stand-alone mode; here, as part of a behind the ear speech processing unit 178. When the recipient or their carer wishes speech processor module 180 to be protected by case 202, ear hook 182 and power supply 184 are detached from speech processor module 180, and the speech processor module is mounted on tray 324 of protective case 202. On-board power supply 216 is also mounted on tray 324. Cover member 206 is then secured to base member 204 to provide a sealed enclosure in which speech processor module 180 and on-board power supply 216 are protected. The resulting external component system 200 is then used in place of the external component assembly 142 illustrated in FIG. 1A. Protective case 202 is secured to the recipient using, for example, strap(s) threaded through brackets 218.

As noted, in one embodiment, an on-board power supply 216 is included in protective case 202 to provide power to speech processor module 180 when the speech processor module is installed in protective case 202. Power supply 216 may be any suitable power supply now or later developed including but not limited to rechargeable batteries. In one embodiment, on-board power supply 216 implements batteries which are conventional, commercially-available batteries, making them significantly less expensive than detachable power supply 184.

Appropriate electrical connections are provided to transfer power from on-board power supply 216 to speech processor module 180. Referring to FIG. 3, speech processor module 180 has one or more connector pins 322 for connecting speech processor module 180 to detachable power supply 184 when implementing the stand-alone operational mode. It should be appreciated that detachable power supply 184 has a connector (not shown) constructed and arranged to mate with the appropriate pin(s) 322 of speech processor module 180 to transfer power.

As shown in FIGS. 2 and 3, when speech processor module 180 is installed in protective case 202, on-board power supply 216 may not directly contact speech processor module 180. As a result, a connector similar to that implemented in detachable power supply 184 is not used in such embodiments to directly connect on-board power supply 216 to speech processor module 180. Rather, in the illustrative embodiment, a bridge connection is provided in protective case 202 to connect the appropriate pin(s) 322 of speech processor module 180 to terminals 328 of on-board power supply 216.

In one embodiment, tray 324 provides the means to electrically connect on-board power supply 216 and speech processor module 180. Tray 324 also comprises apparatus to removably secure an installed power supply 216 and speech processor module 180 to prevent damage to themselves or the other components housed in protective case 202.

In the embodiment shown in FIGS. 2 and 3, on-board power supply 216 is retained between a pair of vertical posts 326. Tray 324 also includes appropriately arranged contacts to electrically mate with terminals 328 on power supply 216 when the power supply is mounted on tray 324. In the embodiment shown, power supply 216 has terminals 328 disposed along a corner of the power supply. Accordingly, tray 324 comprises contacts disposed at the junction of vertical columns 326 and the top surface of tray 324. It should be apparent to those of ordinary skill in the art that the contacts provided in tray 324 to electrically mate with terminals 328 of on-board power supply 216 may be located at any appropriate location and be configured in any way which will achieve a desired electrical connection.

As one of ordinary skill in the art would appreciate, the manner in which on-board power supply 216 is removably mounted on tray 324 can vary depending on a variety of factors including but not limited to the anticipated environment to which external component 200 and, in particular, protective case 202, will be exposed, the weight and mass of power supply 216, the weight distribution of the power supply, etc.

As noted, speech processor module 180 is removably mounted on tray 324. In the embodiment shown in FIG. 3 speech processor module 180 is shown detached from power supply 184 and ear hook 182, exposing pins 322 and raised guide surface 330. Raised guide surface 330 is received by a complementary channel in detachable power supply 184 to cause the power supply to properly mate with pins 322 when the power supply is attached to speech processor module 180.

Tray 324 comprises a connector block 332 having in one embodiment, a mechanical and electrical interface similar to that of detachable power supply 184. That is, connector block 332 comprises a connector (not shown) constructed and arranged to mate with pins 322 when speech processor 180 is mounted on tray 324. In addition, connector block 332 has an integrated channel 320 configured to slidingly receive raised guide surface 330 of speech processor module 180. To mount speech processor module 180 on tray 324, the speech processor module is positioned such that raised guide surface 330 is aligned with an open end of channel 320. As speech processor module 180 is slid into position, channel 320 and raised guide surface 330 cooperate to facilitate the mating of speech processor module 180 and the connector of connector block 332.

In addition, raised guide surface 330 and channel 320 cooperate to securely retain speech processor module 180 to tray 324 when the speech processor module is mounted in protective case 202. It should be appreciated, however, that additional or alternative means may be employed to removably secure speech processor module 180 to tray 324. Embodiments of tray 324 may also include other components to facilitate the removable mounting of speech processor 180. For example, in the embodiment illustrated in FIG. 3, a brace 318 which is curved to abut or be adjacent with a curved surface of speech processor module 180 is provided. In alternative embodiments, speech processor 180 is securely retained in protective case 324 using other techniques now or later developed.

When speech processor module 180 and on-board power supply 216 are mounted on tray 324, they are electrically connected to each other. In the embodiment shown in FIGS. 2 and 3, for example, such electrical connection is provided by tray 324 so that additional components need not be included in protective case 202, and additional steps beyond mounting speech processor 180 and power supply 216 are not necessary to attain an electrical connection.

Specifically, wiring connects the power supply contacts (not shown) on tray 324 and the connector (not shown) on connector block 332 which mates with speech processor module 180. Such wiring may be integrated, for example, into platform 336 of tray 324, or may extend below platform 336. In the latter embodiment, tray 324 preferably does not rest in the bottom surface of base member 204; rather, it rests on support members to provide a space between platform 336 and base member 204 when tray 324 is secured to the base member.

As one of ordinary skill in the art would appreciate, the type of electrical connection provided can vary depending on the particular application. For example, the pins and sockets used to establish the battery connection can be replaced with any other type of electrical connectors. Also, one pin 322 can provide both the positive and ground connections for transferring power to speech processor module 180.

As noted, base member 204 and cover member 206 are attached to each other to provide a protective enclosure for speech processor module 180 and on-board power supply 216. Cover member 206 and base member 204 are configured also to provide the recipient or carer access the enclosure to install or remove speech processor module 180 and power supply 216. In the embodiment shown in FIGS. 2 and 3, for example, cover member 206 is removable; that is, cover member 206 and base member 204 separate from each other to expose the interior of base member 204. It should be appreciated, however, that a portion or all of cover member 206 may be configured, for example, to rotate away from base member 204 to create an aperture through which speech processor module 180 and on-board power supply 216 can be passed. Such rotation can be provided, for example, with mechanical hinges. There are, of course, a myriad of other arrangements that may be implemented to provide the noted access. For example, one or more rotating, sliding, removable, or other types of doors, panels, sides, etc., may be implemented in either or both, cover member 206 and base member 204.

Cover member 206 and base member 204 may be formed of any material or combination of materials suitable for the intended recipient and environment. For example, cover and base members 206, 204 may be formed of metallic material, ceramic material, polymeric material, composites or any combination thereof. In addition, cover and base members 206, 204 may be opaque, translucent, transparent, etc., to provide a desired view of a desired portion of the interior of protective case 202 from the recipient, carer or third party.

In the exemplary embodiment shown in FIG. 3, protective case 202 contains a gasket 302 to seal protective case 202 when cover member 206 is joined with base member 204. As noted, embodiments of protective case 202 protect components mounted therein from a variety of environmental elements such as fluids, dust, etc. Gasket 302 is appropriately configured and formed of the appropriate material to provide the desired degree of protection from at least the environmental elements of concern.

In the embodiment shown in FIGS. 2 and 3, gasket 302 is shaped to be disposed between the mating surfaces of cover member 206 and base member 204 when the cover and base are brought together to form protective case 202. Accordingly, gasket 302 takes the shape of the perimeter of protective case 202 at the location that the cover and base members meet. In one particular embodiment, gasket 302 provides additional protection. As shown in FIGS. 2 and 3, gasket 302 includes a contiguous sheath 334 of fluid-impermeable, resiliently flexible material extending across the interior of the gasket. When installed in protective case 202, this embodiment of gasket 302 seals with the perimeter wall of base member 204. This causes sheath 334 to cover speech processor module 180 and power supply 216 mounted in base member 204. Thus, in addition to preventing ingress of at least selected environmental elements, gasket 302 and sheath 334 also protect components from those environmental elements which manage to penetrate protective casing 202. Sheath 334 can be manufactured from polymeric, elastomeric or other suitable materials. In one embodiment, sheath 334 is transparent.

Protective case 202 comprises a fixation device to removably secure cover member 206 to base member 204. In the embodiment illustrated in FIGS. 2 and 3, such a fixation device comprises a combination of an appropriately located screw and threaded hole. Specifically, sheath 334 has an orifice 304 formed therein that is adapted to allow passage of a threaded shaft of fixation screw 214 through sheath 334. Similarly, cover member 206 has an orifice 308 adapted to allow passage of the threaded shaft of screw 214. When cover member 206 and sheath 334 are assembled with based member 204, orifice 308 and orifice 304 are aligned with each other. Screw 214 may then pass through orifice 308 in cover member 206, and orifice 304 in sheath 334 to threadingly engage a threaded hole 310 of a post 312 on tray 324.

It should be appreciated by those of ordinary skill in the art that the implemented fixation device should not degrade the integrity of the protective features implemented in protective case 202. For example, in the above embodiment in which a fixation screw 214 is implemented, at the location of screw 214, an elastomeric grommet 314 is provided to help prevent ingress of fluid into the protective case at the site of screw 214. Additionally washers, o-rings and the like may also be used as appropriate.

External component system 200 also comprises a one-piece headpiece 208 communicably coupled to speech processor module 180 via a cable 210. As noted, headpiece 208 comprises the above-noted external transmitter unit 106 including external coil 108, and magnet 110 mounted in a housing 220 that provides the same or similar protection of its components as protective case 202.

In accordance with one embodiment of the present invention, headpiece 208 also comprises a second microphone 212 mounted thereon which is operable when speech processor module 180 is installed in protective case 202. When speech processor module 180 is installed in protective case 202, microphone 186 cannot be used since it will be enclosed with protective case 202. As such, external component system 200 provides an alternate or replacement microphone 212, referred to as external microphone 212.

Protective case 202 has an additional orifice (not shown) provided in base member 204 to permit cable 210 to be inserted into the case. Cable 210 extends from headpiece 208 into case 202 to mate with connector 188 of speech processor module 180. The orifice may be sealed, for example, by a grommet 316 provided around the distal end of cable 210. For example, in one embodiment, grommet 316 and orifice are constructed and arranged to prevent water from entering protective case 202.

As noted, protective case 202 provides protection for speech processor module 180 and on-board power supply 216. In the embodiments described above, such protection includes protecting the components from ingress of fluid, dust or other particulates such as airborne fumes. In other embodiments, protective case 202 is capable of providing protection against electromagnetic interference (EMI). In such embodiments, the interior surfaces of cover member 206 and base member 204 are coated with a conformal EMI coating such as that used in cellular phones, computer systems and other electronic devices that emit or are sensitive to electromagnetic radiation. In addition, in such embodiments gasket 302 is an EMI gasket suitable for preventing EMI from escaping through the joined surfaces of cover member 206 and base member 204.

In other embodiments, protective case 202 protects the components mounted therein from vibration and/or shock. In such embodiments, tray 324 may be suspended on a shock- and vibration-absorbing material or elements such as resilient posts or extensions disposed in or integrated with base member 204. In addition, the dimensions of tray 324 may be somewhat less than the interior dimensions of protective case 202 to reduce the likelihood of shocks to tray 324 and the components mounted thereon.

Figure 4:
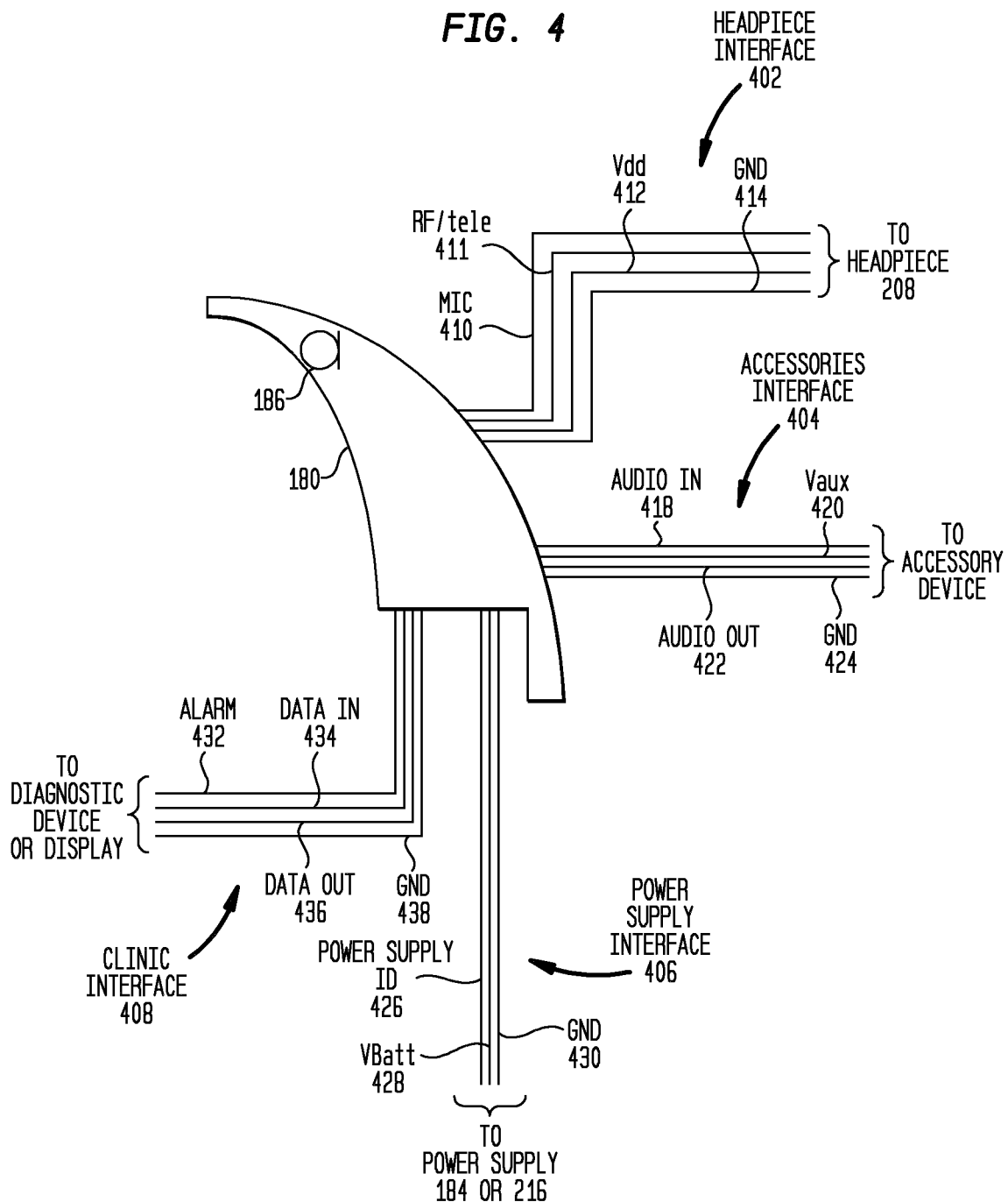
FIG. 4 is an interface diagram of one embodiment of the speech processor module illustrated in FIG. 1B.

FIG. 4 is a schematic interface diagram of one embodiment of speech processor module 180 illustrated in FIGS. 2 and 3. In the embodiment shown in FIG. 4, speech processor module 180 comprises four (4) interfaces, a headpiece interface 402, an accessories interface 404, a power supply interface 406, and a clinical/diagnostic interface 408. Each of the interfaces 402-408 is supported by one or more connectors as described above with references to FIGS. 2 and 3. It should be appreciated by those of ordinary skill in the art, however, that interfaces 402-408 may be implemented in one or more connectors configured differently than that described herein.

Headpiece interface 402 comprises a microphone signal line 410, an RF/telemetry signal line 411, a voltage signal line 412 and a ground signal line 414. In the embodiment shown in FIGS. 2 and 3, these signal lines are included in cable 210 connecting headpiece 208 and speech processor module 180 via connector 188.

Accessories interface 404 comprises an input audio signal line 418, an auxiliary voltage input signal line 420, an output audio signal line 422 and a ground signal line 424. These signal lines are transmitted between an accessory device (not shown) and accessories connector 190 of speech processor module 180.

Power supply interface 406 comprises a power supply identifier (ID) signal line 426, a voltage signal line 428, and a ground signal line 430. These signal lines are transmitted between one or more pins 322 of speech processor module 180 and either power supply 184 or power supply 216.

Clinical/diagnostic interface 408 comprises an alarm signal line 432, data in and out signal lines 434, 436, and a ground signal line 438. These signal lines are transmitted between one or more pins 322 of speech processor module 180 and a diagnostic device or display (not shown).

It should be appreciated that in the embodiment of external component system 200 illustrated in FIGS. 2 and 3, the apertures in protective case 202 which provide access by cables that connect to accessory connector 190 (providing accessory interface 404), and pin(s) 322 (providing clinical interface 408) are not shown. Such apertures, however, are the same or similar to those described above. In an alternative embodiment, such interfaces are available only when speech processor module 180 implements the stand-alone mode of operation.

Figure 5:
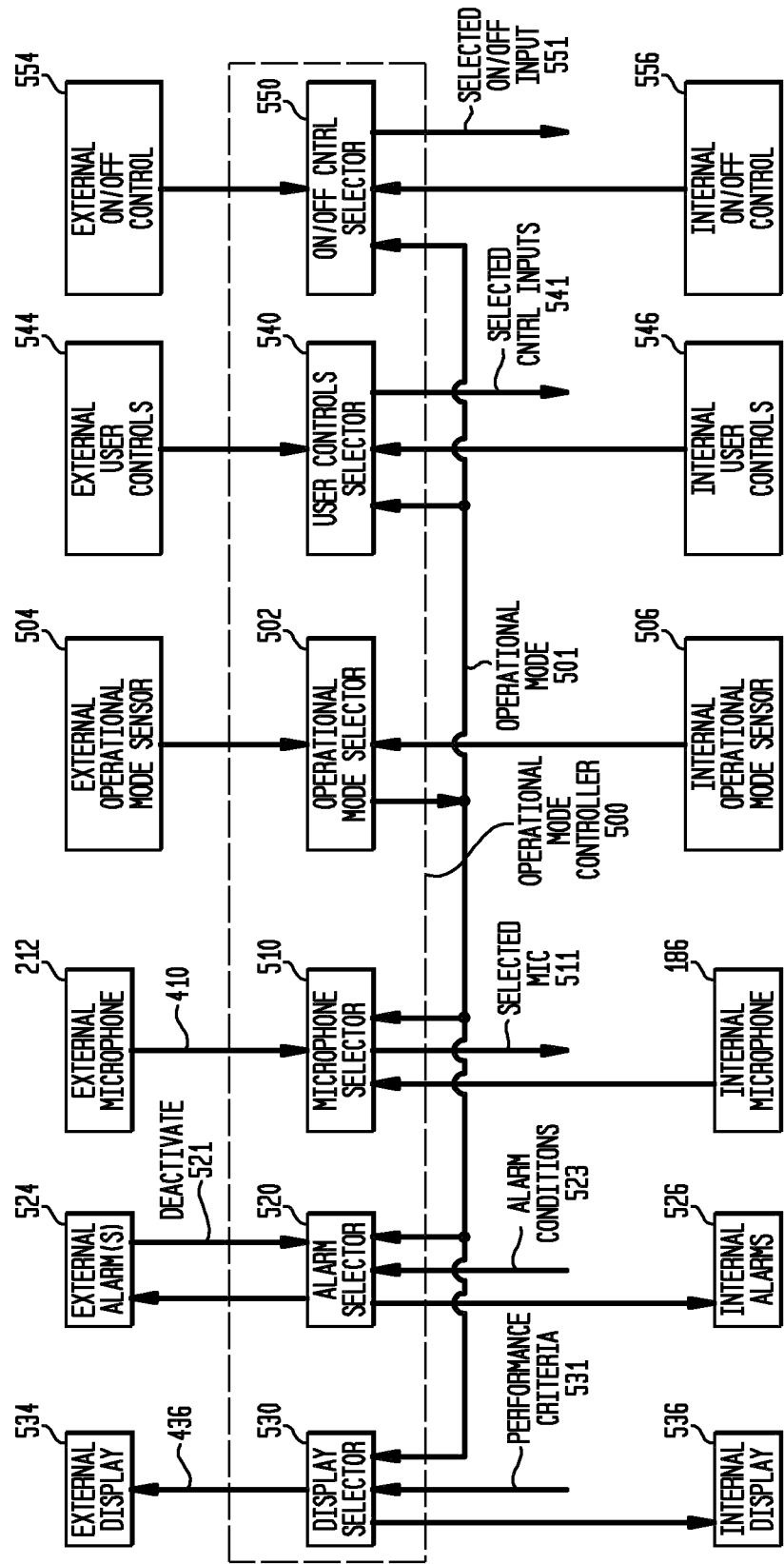
FIG. 5 is a functional block of one embodiment of an aspect of the present invention.

FIG. 5 is a functional block diagram of these components of the present invention which enable speech processor module 180 to transition between stand-alone and a body-worn operational modes. In FIG. 5 an operational mode controller 500 is implemented in speech processor module 180 to determine which operational mode speech processor module 180 is to implement, and to select the appropriate internal inputs and outputs (that is, provided as part of speech processor module 180) and external inputs and outputs (that is, provided as part of external component system 200) to enable speech processor module 180 to function in the desired operational mode.

Figure 6A:
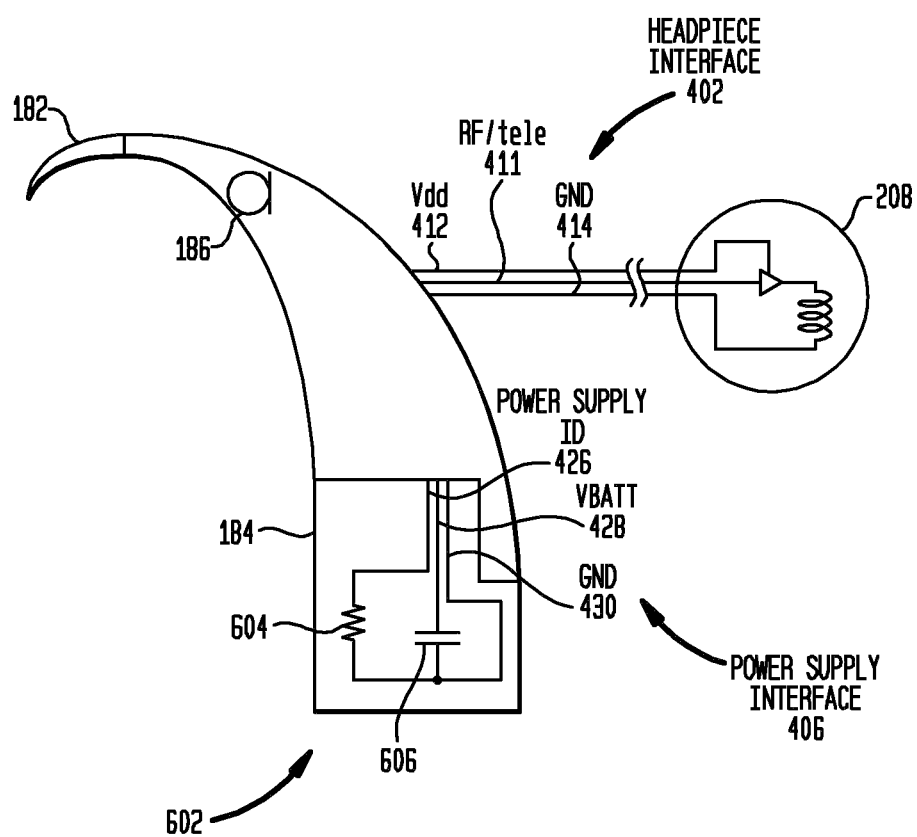
FIG. 6A is a schematic diagram of the relevant signal and electrical interfaces when the speech processor module shown in FIG. 1B is implemented in a stand-alone operational mode.
Figure 6B:
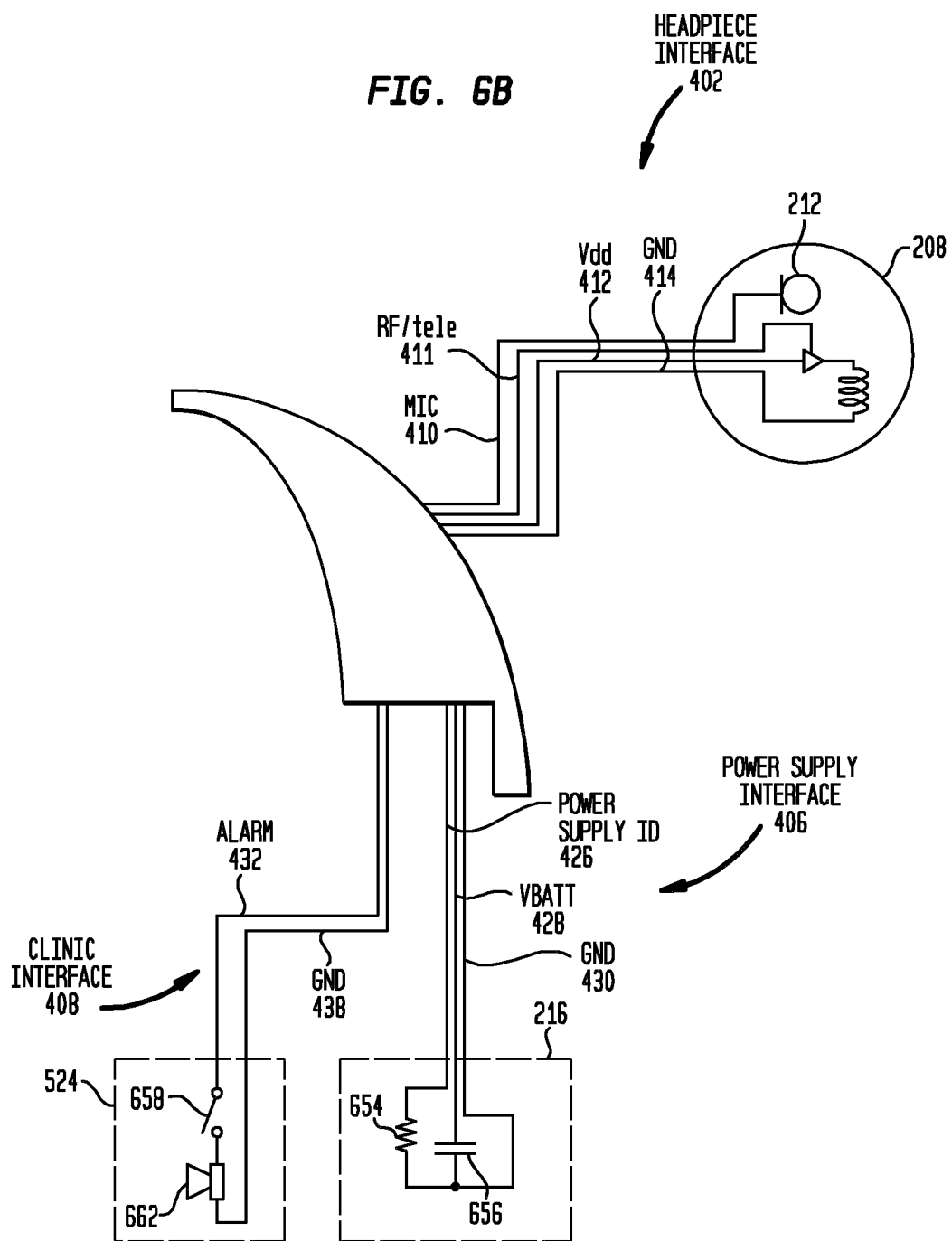
FIG. 6B is a schematic of the relevant signal and electrical interfaces when the speech processor module shown in FIG. 1B is implemented in a body-worn operational mode.

FIGS. 6A and 6B are schematic diagrams showing a portion of the interfaces utilized by one embodiment of speech processor module 180 when implemented in both modes of operation. In FIG. 6A, speech processor module 180 has ear hook 182 and power supply 184 attached to facilitate, in this embodiment, use as a stand-alone behind-the-ear (BTE) speech processing unit 178. Detachable power supply 184 is shown schematically, and contains a rechargeable battery 606 and an identifier resistor 604. Detachable power supply 184 is connected to speech processor module 180 via power supply interface 406. External coil 208, also shown schematically, is connected to speech processor module 180 via headpiece interface 402. It should be appreciated, however, that when in the BTE operating mode, speech processor module 180 does not utilize external microphone 212, and external transmitter unit 106 (FIG. 1A) may be used with speech processor module 180 rather than exterior component system 200.

In FIG. 6B, speech processor module 180 is not attached to ear hook 182 and power supply 184. Rather, it is coupled to on-board power supply 216 and an alarm system 524. As will be described in detail below, speech processor module 180 may be connected to a variety of external components implemented in protective case 202 or other components of external component system 200 depending on the implemented functionality. The embodiment shown in FIG. 6B is just one exemplary implementation. In addition, external coil 208, also shown schematically, is connected to speech processor module 180 via headpiece interface 402 in the arrangement shown in FIG. 6B.

Returning to FIG. 5, in accordance with one embodiment of the present invention, operation mode controller 500 comprises an operational mode selector 502 that determines which operational mode speech processor module 180 is to implement. As noted, in the exemplary embodiment described herein, speech processor module 180 may be implemented in a stand-alone mode as illustrated in FIG. 1B, or a body-worn mode of operation as illustrated in FIGS. 2 and 3.

Operational mode selector 502 makes the noted determination based on settings or conditions sensed or received by either an external operational mode sensor 504 implemented in protective case 202, or an internal operational mode sensor 506 implemented in speech processor module 180.

In one embodiment, the operational mode of speech processor module 180 is determined based on the identification of the power supply that is connected to the speech processor module. In such an embodiment, each power supply which may be utilized in connection with speech processor module 180 includes some identifying feature. Information regarding the identifying feature is communicated to speech processor module 180 via power supply identification (ID) signal line 426. In such embodiments, an internal operational mode sensor 506 is implemented to detect the particular identifying feature.

For example, in the embodiment illustrated in FIGS. 6A and 6B, the identifying feature is the value of a resistor included in each power supply. Referring to FIG. 6A, detachable power supply 184 comprises a resistor 604 and, in this example, a rechargeable battery 606. Resistor 604 identifies power supply 184 as a type of detachable power supply suitable for use when speech processor module 180 implements the stand-alone mode of operation. Referring to FIG. 6B, on-board power supply 216 comprises a resistor 654 and, in this example, a rechargeable battery 656. Resistor 654 identifies power supply 216 as a type of on-board power supply suitable for use when speech processor module 180 implements the body-worn mode of operation.

In such embodiments, internal operational mode sensor 506 measures the resistance between ID signal line 426 and ground signal line 430 to determine the resistance of resistor 604 or 654. Based on this information, the type of power supply (i.e. one suitable for use in stand-alone mode verse one suitable for use in body-worn mode), and the desired mode of operation is determined by operational mode selector 502. The operational mode 501 is then distributed to other functional components of controller 500 as described herein.

It should also be appreciated that operational mode sensors 504, 506 may utilize other information to determine the operational mode of speech processor module 180. For example, an externally-accessible switch may be provided on speech processor unit 180 (as part of internal sensor 506) or protective case 202 (as part of external sensor 504) to enable the recipient or another to manually select the operational mode. When implemented as part of external sensor 504, such a switch is preferably configured to prevent infants and children from changing the operational mode, as well as to prevent accidental changing of the operational mode during the intended use of the body-worn external component system 200. When implemented as part of internal sensor 506, such a switch is inaccessible once speech processor module 180 is mounted in protective case 202 making such safeguards optional.

In another embodiment, external operational mode sensor 504 includes an infrared or other sensor responsive to signals transmitted by a remote control device. Such an embodiment allows the recipient or their carer to transmit appropriate signals to select the desired operational mode of speech processor module 180.

Based on the selected mode of operation 501 generated by operational mode selector 502, a microphone selector 510 of controller 500 selects which microphone to use. When in the stand-alone mode of operation, internal microphone 186 is utilized, as shown in FIG. 6A. When implementing the body-worn mode of operation, microphone 212 on headpiece 208 is utilized, as shown in FIG. 6B. Microphone selector 510 forwards, connects, routes or otherwise provides the selected microphone 511 to other components of speech processor module 180.

As one of ordinary skill in the art would appreciate, external microphone 212 may be located elsewhere; however, it is preferable that the external microphone be integrated into headpiece 208 as described herein. Such an embodiment reduces the quantity of components while also protecting the external microphone.

In the embodiment shown in FIG. 5, speech processor module 180 comprises internal alarm(s) 526 to provide the recipient or another with visual and/or audible indications of predetermined conditions occurring in the speech processor module when the speech processor module implements the stand-alone mode of operations. Exterior alarm(s) 524 are provided in protective case 202 to provide the same or similar alarms to the recipient or another when speech processor module 180 implements the body-worn mode of operation. In accordance with one embodiment, operational mode controller 500 comprises an alarm selector 520 that selects whether alarm conditions are to be broadcast using internal alarms 526 or external alarms 524 based on the selected operational mode 501.

Referring to FIG. 6B, external alarm(s) 524 is/are implemented in protective case 202 and comprises a buzzer 662 that is actuated when an alarm condition 523 is detected. External alarm(s) 524 incorporate a switch 658 that can be thrown by the recipient or another to generate a deactivate signal 521 to disable the alarm function. Such a switch is preferably configured to prevent the unintended changing of the state of the alarm.

In one embodiment, external alarm 524 is implemented as part of connector block 332 on tray 324. In an alternative embodiment, external alarm 524 is implemented elsewhere on tray 324 or in protective case 202. It should be understood that the above embodiment of external alarm 524 is a buzzer. Such an audible alarm may be located at the exterior surface of protective case 202, or may be located internal to protective case 202 with an adjacent aperture in the protective case to permit the sound to travel out of the case and be heard by the recipient. In such alternative embodiments, such an aperture is constructed and arranged to provide a degree of protection analogous to that implemented in the other components and aspects of body-worn external components 200.

It should also be appreciated that the type of alarm may include visual indicators in addition to or instead of the audible alarm noted above. Alternatively, an audible sound may be injected into the audio path to be heard by only the recipient. In one embodiment, the type of external alarm (indicator, enunciator, internal audio, etc.), may be selected by the recipient or another, depending on the recipient and intended use of external components 200.

As one of ordinary skill in the art would find apparent, any condition may be selected to be one which qualifies as an alarm condition. For example, in one embodiment, alarm conditions include when the transcutaneous RF link fails such as by displacement of the external antenna. In another embodiment, alarm conditions include when protective case 202 is opened. It should also be appreciated that a hierarchical arrangement of alarm conditions may be established, each having a unique identifying alarm.

Speech processor module 180 comprises an internal display 536 comprising, for example, a liquid crystal display (LCD) and/or one or more LEDs that display performance criteria 531 of the module. In one embodiment, performance criteria 531 comprises battery charge state, memory state, and/or other criteria.

In one embodiment, such performance criteria is not provided to the recipient when speech processor module 180 is mounted in protective case 202. In an alternative embodiment, a portion of cover member 206 and/or base member 204 are transparent to provide a view into a protective case 202 such that internal display 536 can be seen from a position external to protective case 202.

In a further embodiment, illustrated in FIG. 5, protective case 202 provide an external display 534, for example, an LCD display located in cover member 206. A display selector 530 determines whether internal display 536 implemented in speech processor module 180 or external display 534 implemented in protective case 202 is to be used to provide the recipient or another with an indication of the noted performance criteria. Such a determination is based on selected operational mode 501 generated by operational mode selector 501. Such information may be provided to external display 534 via, for example, data out signal line 436.

Speech processor module 180 also comprises internal user controls 546 through which a recipient or another can program or otherwise select functional operating parameters in speech processor module 180. For example, in one embodiment, speech processor module 180 comprises internal user controls 546 which enable, for example, program selection, volume control, etc.

In one embodiment, such user controls are not provided to the recipient when speech processor module 180 is mounted in protective case 202. In a further embodiment, illustrated in FIG. 5, protective case 202 provides external user controls 544 located, for example, in cover member 206 and/or base member 204. A user controls selector 540 determines whether internal user controls 546 of speech processor module 180 or external user controls 544 in protective case 202 are to be utilized to provide the recipient or another with the ability to control speech processor module 180. Such a determination is made based on the operational mode 501 provided by operational mode selector 502.

When external user controls 544 is selected (i.e. speech processor module 180 implements the body-worn mode of operation), the transfer of information from the external interface is provided to selector 540 via, for example, data in signal line 434 (FIG. 4). The user control inputs 541 generated by the selected user controls 544, 546 are forwarded, routed or otherwise provided to speech processor module 180 by selector 540.

Speech processor module 180 includes internal on/off control 556, typically implemented as a manual switch in the housing of the speech processor module which can be manipulated by the recipient or another. When speech processor module 180 is mounted in protective case 202, internal on/off control 556 is no longer accessible to control the power state of speech processor module 180.

In one embodiment, no additional controls are provided. In such an embodiment, protective case 202 must be opened to provide access to the above-noted on/off switch 556 on speech processor module 180. However, such an embodiment is inconvenient and time consuming to manage. In addition, repeated access to protective case 202 will accelerate the wearing of gasket 302 or other seal implemented in protective case 202 to provide the above-noted protection.

In another embodiment, shown in FIG. 5, an external on/off control 554 is included in protective case 202 which can be activated without having to access the internal enclosure of the protective case. In one embodiment, external on/off control 554 includes a reed switch or other magnetically-responsive component implemented in protective case 202. In the illustrated embodiment, the external on/off control 554 generates a signal which is forwarded, routed, passed, regenerated or otherwise provided to a power relay or other component speech processor module 180 to interrupt power to the module. In an alternate embodiment, the magnetically-responsive component is electrically interposed between on-board power supply 216 and speech processor module 180. In this embodiment, speech processor module 180 is disconnected from the power supply when the magnetic field of a magnet such as alignment magnet 110 within headpiece 208 is brought to a location adjacent to the magnetically-responsive switch.

Other embodiments are also configured to cease operation when the transcutaneous RF link has been broken. For example, in one embodiment, internal on/off control 556 causes speech processor module 180 to periodically transmit an RF signal to implantable components 144, and wait for a response. When no response is present, speech processor module 180 enters a standby mode or turns off. If a standby mode is implemented, speech processor module 180 periodically transmits an RF signal while in the standby mode. If a response is received, speech processor module 180 then fully activates, starts processing sound and retransmits signals to implantable component 144.

In another embodiment, external on/off control module 554 can include a manually-activated switch located on the exterior of protective case 202. Such a switch is preferably configured to prevent children from changing the power state, and from accidental changing of the power state during the intended use of the body-worn external components 200.

In addition to one or more of the above embodiments, speech processor module 180 can also be adapted to shut down whenever on-board power supply 216 is being charged. In such an embodiment, protective case 202 also comprises charging circuitry (not shown) to allow power supply 216 to be recharged when case 202 is not in use.

In another embodiment, external on/off control 554 includes an infrared or other sensor responsive to signals transmitted by a remote device operated by the recipient or their carer.

In the case of adults, the present invention provides a recipient with the flexibility of using their speech processor module 180 in a moist environment. For infants and small children, the present invention also can be used in the comfort that the speech processor is less likely to be damaged than would be the case where the speech processor unit is used in the stand-alone mode. The case 202 is also potentially advantageous in that it can serve to assist in preventing tampering of speech processor module 180 by a child recipient or a third party.

What is claimed is:

1. A device, comprising:
a speech processor of a hearing prosthesis; and
a barrier configured to protect the speech processor from water, wherein
the speech processor is part of a behind-the-ear (BTE) device,
the barrier includes an interior compartment in which is located the speech processor,
the barrier protects against ingress of water into the interior compartment, and
a transcutaneous transfer coil assembly is in electrical communication with the speech processor through an opening in the protective barrier.

2. The device of claim 1, wherein the barrier includes two sections configured to be moved relative to one another, so that the barrier can be opened and closed so that the speech processor can be removed therefrom and installed therein, and wherein the device is configured such that when the two sections are brought into proximity with one another to protect the speech processor from water, a seal is established between the two sections preventing water from entering the barrier and reaching the speech processor, and wherein a first section of the two sections is sized and dimensioned to securely retain the speech processor in the first section.

3. The device of claim 1, wherein:
the transcutaneous transfer coil assembly includes a cable that has a distal end at which is located a sealing component that seals the opening in the barrier, wherein the sealing component and the barrier are constructed and arranged to prevent water from entering into the interior compartment.

4. A device, comprising:
a speech processor of a hearing prosthesis; and
a barrier configured to protect the speech processor from water, wherein
the speech processor is part of a behind-the-ear (BTE) device, and
the device further comprises:
a transcutaneous transfer coil assembly including a transcutaneous transfer coil and a cable, wherein
the device is configured to place the transcutaneous transfer coil into signal communication with the speech processor via the cable by way of a connection extending through a dedicated orifice in the barrier.

5. The device of claim 4, wherein:
the barrier is a protective case; and
the speech processor is removably received in the protective case.

6. The device of claim 4, wherein:
at least a portion of a body of the BTE device including the speech processor is removably received in the barrier;
the at least a portion of a body of the BTE device is secured in the barrier by structure of the barrier; and
the barrier protects the at least a portion of the body of the BTE device in the barrier from water.

7. The device of claim 6, wherein:
the barrier includes an interior compartment in which the least a portion of the body of the BTE device is located; and
the barrier protects against ingress of water into the interior compartment.

8. The device of claim 6, wherein:
the barrier is configured to protect against substantially all fluid ingress into the barrier.

9. The device of claim 6, wherein:
the BTE device is configured to enable the evocation of a first hearing percept when the BTE device is located behind an ear of a recipient away from the barrier and when the BTE device is in signal communication with the transcutaneous transfer coil assembly including a transcutaneous transfer coil which is in signal communication with another coil of an implanted hearing prosthesis implanted the recipient; and
the at least a portion the body of the BTE device including the speech processor is configured to enable the evocation of a second hearing percept when the at least a portion of a body of the BTE device is located in the barrier when the at least a portion of a body of the BTE device is in signal communication with the transcutaneous transfer coil assembly including a transcutaneous transfer coil which is in signal communication with the another coil of the implanted hearing prosthesis implanted in the recipient.

10. The device of claim 4, wherein:
the barrier includes a main housing and a lid, the barrier including a gasket that seals an interior of the barrier from an exterior of the barrier; and
the speech processor is removably received in the barrier and the gasket seals the barrier.

11. The device of claim 4, wherein:
the barrier is transparent.

12. The device of claim 4, wherein:
the transcutaneous transfer coil assembly is configured to mate with a connector of the speech processor, wherein the transcutaneous transfer coil assembly and the barrier are constructed and arranged to prevent water from entering into an interior of the barrier.

13. A device, comprising:
a speech processor of a hearing prosthesis; and
a barrier configured to protect the speech processor from water, wherein
the speech processor is part of a behind-the-ear (BTE) device,
the BTE device includes a body, at least a portion of the body including the speech processor, the at least a portion of the body being configured to be removably received in the barrier, and
the barrier includes two sections configured to be moved relative to one another, so that the barrier can be opened and closed so that the at least a portion of the body of the BTE device can be removed and installed therein, and wherein the barrier is configured so that when the two sections are brought into proximity with one another to protect the at least a portion of the body of the BTE device from water, a seal is established between the two sections preventing water from entering the barrier and reaching the speech processor, and wherein the barrier includes an opening through which an electrical communication component extends, placing the body of the BTE device in signal communication with a transcutaneous transfer coil outside the barrier.

14. The device of claim 13, wherein:
the at least a portion of the body of the BTE device including the speech processor is removably received in the barrier; and
the device further comprises:
a transcutaneous transfer coil assembly including the transcutaneous transfer coil and a cable connected to the transcutaneous coil, wherein the transcutaneous transfer coil is in signal communication with the speech processor via a connector connected to the cable at a distal end of the cable the connector extending through the opening, the connector corresponding to the electrical communication component.

15. The device of claim 13, wherein:
the transcutaneous transfer coil is in signal communication with the speech processor via the electrical communication component, and
the device is configured to enable the evocation of a hearing percept when the at least a portion of the body of the BTE device is located in the barrier when the at least a portion of the body of the BTE device is in signal communication with the transcutaneous transfer coil located outside the barrier which is in signal communication with another coil of an implanted hearing prosthesis implanted in a recipient.

16. A device, comprising:
a speech processor of a hearing prosthesis; and
a barrier configured to protect the speech processor from water, wherein
the speech processor is part of a behind-the-ear (BTE) device, and
the device further comprises a transcutaneous transfer coil assembly including a coil and a housing, wherein the housing of the transcutaneous transfer coil assembly provides the same protection to at least one functional component of the transcutaneous transfer coil assembly as the barrier does to the speech processor, wherein the coil is located outside the barrier and the speech processor is located inside the barrier, and wherein the barrier includes an opening through which a jack extends, the jack placing the transcutaneous transfer coil assembly into signal communication with an interior of the barrier.

17. The device of claim 16, wherein:
the barrier includes a first portion configured to move relative to a second portion of the barrier to open and close the barrier to enable installation and removal of the speech processor, wherein the first portion and second portion of the barrier form an interior in which the speech processor is located and protected from water by a seal between the first portion of the barrier and the second portion of the barrier, wherein the second portion is sized and dimensioned to hold the speech processor in the barrier.

18. The device of claim 16, wherein:
the barrier is configured to prevent substantially all fluid ingress at elevated atmospheric pressures.

19. A device, comprising:
a behind-the-ear (BTE) component including a speech processor of a hearing prosthesis; and
a protective barrier, wherein the protective barrier is a protective barrier for the BTE component including the speech processor of the hearing prosthesis, the protective barrier including:
a main body having a hollow portion configured to receive the BTE component; and
a lid configured to extend over the hollow portion of the main body, wherein
the protective barrier is configured to removably receive the BTE component and protect the BTE component from water,
the BTE component is removably received in the protective barrier, and the protective barrier protects against substantially all fluid ingress into the protective barrier, and
the barrier is configured to enable a connector of a cable to mate with the BTE component with the cable located outside the barrier and thus mate with the speech processor that is a part of the BTE component while the BTE component is located in the barrier such that the BTE component is protected from water.

20. The device of claim 19, wherein:
the protective barrier is transparent.

21. A device, comprising:
a behind-the-ear (BTE) component including a speech processor of a hearing prosthesis; and
a protective barrier, wherein the protective barrier is a protective barrier for the BTE component including the speech processor of the hearing prosthesis, the protective barrier including:
a main body having a hollow portion configured to receive the BTE component; and
a lid configured to extend over the hollow portion of the main body, wherein
the protective barrier is configured to removably receive the BTE component and protect the BTE component from water,
the BTE component is removably received in the protective barrier, and the protective barrier protects against substantially all fluid ingress into the protective barrier, and
the protective barrier is configured to enable a connector of a cable to directly mate with the BTE component and the speech processor that is a part thereof while the BTE component is located in the barrier such that the BTE component is protected from water, thus providing electrical communication from the speech processor to a location outside the protective barrier.

22. The device of claim 21, wherein:
the protective barrier is configured to retain the BTE component on one side of the hollow portion relative to an opposite side of the hollow portion.

23. A device, comprising:
a behind-the-ear (BTE) component including a speech processor of a hearing prosthesis; and
a protective barrier, wherein the protective barrier is a protective barrier for the BTE component including the speech processor of the hearing prosthesis, the protective barrier including:
a main body having a hollow portion configured to receive the BTE component; and
a lid configured to extend over the hollow portion of the main body, wherein
the protective barrier is configured to removably receive the BTE component and protect the BTE component from water,
the BTE component is removably received in the protective barrier, and the protective barrier protects against substantially all fluid ingress into the protective barrier, and
the protective barrier is configured to prevent substantially all fluid ingress at elevated atmospheric pressure when the lid is closed, and wherein an opening for a communications jack is located in the protective barrier.

24. The device of claim 23, further comprising:
a transcutaneous transfer coil assembly including a transcutaneous transfer coil and a cable and the communications lack, wherein
the transcutaneous transfer coil is in signal communication with the BTE component via the cable by way of the communications jack extending through the opening for the communications jack located in the protective barrier,
the transcutaneous transfer coil assembly has mated with a connector of the BTE component via the communications jack, and the transcutaneous transfer coil assembly and the barrier are constructed and arranged to prevent water from entering the protective barrier.

25. A device, comprising:
a behind-the-ear (BTE) component including a speech processor of a hearing prosthesis; and
a protective barrier, wherein the protective barrier is a protective barrier for the BTE component including the speech processor of the hearing prosthesis, the protective barrier including:
  a main body having a hollow portion configured to receive the BTE component; and
  a lid configured to extend over the hollow portion of the main body, wherein
the protective barrier is configured to removably receive the BTE component and protect the BTE component from water,
the BTE component is removably received in the protective barrier, and the protective barrier protects against substantially all fluid ingress into the protective barrier, and
the protective barrier is configured to enable the lid to move relative to the main body to open and close the protective barrier, wherein the main body and the lid form an interior in which, when the BTE component is removably received therein, the BTE component is protected from water by a seal between the main body and the lid, and wherein the main body is sized and dimensioned to securely hold the BTE component therein.

26. The device of claim 25, wherein:
the protective barrier is configured to enable a connector of a cable connected to a transcutaneous transfer coil to be inserted through an orifice of the protective barrier to establish communication between the cable and a connector of the BTE component while protecting the BTE component from water such that a hearing percept can be evoked by an implanted component based on speech processed by the speech processor of the BTE component using the transcutaneous transfer coil via communication between the transcutaneous transfer coil and the speech processor while the BTE component is located in the protective barrier such that the BTE device is protected from water.

27. The device of claim 25, wherein:
a connector of a cable connected to a transcutaneous transfer coil is inserted through an orifice in the protective barrier and has established communication between the cable and a connector of the BTE component while the protective barrier protects the BTE component from water such that a hearing percept can be evoked by an implanted component based on speech processed by the speech processor of the BTE component using the transcutaneous transfer coil via communication between the transcutaneous transfer coil and the speech processor while the BTE component is located in the protective barrier such that the BTE component is protected from water.

28. A method of utilizing an external component of a cochlear implant hearing system, the method comprising:
operating a speech processor module of the external component of the cochlear implant in a stand-alone mode;
removably placing the speech processor module in an external device configured to have said speech processor module removably located therein and configured to protect the speech processor module from water;
placing a transcutaneous communication assembly that is located outside the external device into signal communication with the speech processor module in the external device by passing a jack of the transcutaneous communication assembly through an opening in the external device;
placing the transcutaneous communication assembly into signal communication with an implanted portion of the cochlear implant hearing system; and
operating the speech processor module in the external device to cause the implantable portion of the cochlear implant hearing system to evoke a hearing percept, wherein
the jack includes a component provided around a distal end of a cable of the transcutaneous communication assembly that prevents water from entering the external device.

* * * * *